United States Patent [19]

Amiot et al.

[11] Patent Number: 5,202,254

[45] Date of Patent: Apr. 13, 1993

[54] PROCESS FOR IMPROVING MASS TRANSFER IN A MEMBRANE BIOREACTOR AND PROVIDING A MORE HOMOGENEOUS CULTURE ENVIRONMENT

[75] Inventors: Bruce P. Amiot, Roseville, Minn.; Martin H. Banas, Modesto, Calif.; Allen S. Reichler, Indianapolis, Ind.; Scott T. Waniger, Andover

[73] Assignee: Endotronics, Inc., Minneapolis, Minn.

[21] Appl. No.: 595,939

[22] Filed: Oct. 11, 1990

[51] Int. Cl.⁵ .................. C12N 5/00; C12N 5/02; C12M 1/18

[52] U.S. Cl. .................. 435/240.242; 435/240.1; 435/240.241; 435/240.25; 435/300

[58] Field of Search .................. 435/240.1, 240.241, 435/240.242, 240.25, 289, 300

[56] References Cited

U.S. PATENT DOCUMENTS 4,680,267 7/1987 Eppstein .................. 435/289
4,889,812 12/1989 Guinn et al. .................. 435/289
4,937,194 6/1990 Pattillo .................. 435/240.241

OTHER PUBLICATIONS

Tharakan et al Biotechnology and Bioengineering vol. XVII pp. 329-342 (1986).
Robertson et al Biotechnology and Bioengineering vol. XXVII pp. 1012-1020 (1985).

Primary Examiner—Douglas W. Robinson
Assistant Examiner—Jane A. Williams
Attorney, Agent, or Firm—Sughrue, Mion, Zinn, Macpeak & Seas

[57] ABSTRACT

A process for improving mass transfer in a bioreactor having at least one semi-permeable membrane defining first and second chambers on opposite sides of the membrane provides for circulating a first media including nutrients and the like through the first chamber and for circulating a second media for cell culture through the second chamber of the bioreactor. The first and second media may be circulated through a plurality of bioreactors connected in parallel while balancing the flow in each reactor. The flow in the second circuit can be periodically reversed to provide increased cell culture.

4 Claims, 3 Drawing Sheets

PROCESS FOR IMPROVING MASS TRANSFER IN A MEMBRANE BIOREACTOR AND PROVIDING A MORE HOMOGENEOUS CULTURE ENVIRONMENT

BACKGROUND OF THE INVENTION

The present invention is directed to a process for culturing cells in a bioreactor having semi-permeable membranes and more specifically, to a process involving the provision of circulation means on the cell side of the membranes to improve mixing and reduce boundary layers and concentration gradients along the membranes and in and/or around the cell mass to improve mass transfer.

Cell culture devices for culturing cells in vitro having a shell with a plurality of hollow fiber membranes have been known for quite some time. Media containing oxygen, nutrients and other chemical stimuli is transported through the lumen of the hollow fiber membranes and undergoes a pressure drop resulting in an outward radial convective flow at the entry port of the device and an inward flow at the exit port of the device. Cells are grown in the fluid space between the fibers and the shell wall. Cell culture devices using sheet membrane bioreaactors are also well known and work as well as hollow fiber membranes.

Hollow fiber culture devices have been proven to be ideal for the maintenance of many types of cells at high densities in vitro. The mass transfer characteristics of hollow fiber culture devices provide an efficient means for delivering nutrients and removing waste products from a culture. The semi-porous, hollow fiber membranes can be selected with various pore sizes. With proper pore size selection, the cellular product can be maintained on the outside of the fibers while waste products and contaminating proteins will pass through the membrane pores into the lumen of the hollow fibers where they can be subsequently removed from the culture. In the use of such conventional hollow fiber techniques, the extracapillary space is capped or dead-ended at both ends. This creates a Starling effect and a heterogeneous environment. Cells generally grow only toward the proximal end of the bioreactor. Also, large molecular weight components trapped in the extracapillary space concentrate at the distal end.

To economically produce cell-derived products in a hollow fiber device, large numbers of the cells must be maintained viable in optimal culture conditions for product formation over long periods of time. Prior art hollow fiber culture devices have many limitations that prevent their use in the economical production of cell-derived products in commercial quantities. These limitations include:

1) formation of gradients in the cell compartment;
2) inability to directly monitor and control cellular environment;
3) lack of fluid movement in cell compartment leads to microenvironment formation around cells;
4) fibers are not equidistant apart in culture device leading to anoxic or dead spaces;
5) efficient mass transfer becomes difficult at high cell densities; and
6) the pressure drop across the device increases as the pressure is scaled up, increasing the problems cited above, thus limiting scaleability.

The purpose of the present invention is to overcome these limitations, making it possible to utilize a hollow fiber culture device or other conventional sheet membrane devices for the economical production of cell-derived products In order to overcome the foregoing limitations, it was proposed in the Cracauer et al. U.S. Pat. No. 4,804,628 to provide an expansion chamber connected to opposite ends of the extracapillary space by cell culturing units such as a hollow fiber cartridge in which the cells are maintained and grown. The hollow fiber cartridge included a plurality of capillaries extending through a shell with each capillary including a lumen through which media containing oxygen, nutrients and other chemical components are transported. A delivery system or integration circuit delivers a primary media supply through the lumens of the capillaries of the bioreactor as shown in the prior art schematic diagram in FIG. 2. The integration circuit includes a pump for circulating the media through the integration circuit. A gas exchange cartridge, a DO probe, a pH probe, and an integration chamber may also be included in the integration circuit.

The extracapillary circuit containing the expansion chamber may be provided with valves between the expansion chamber and the extracapillary space. By regulating pressure differences between the integration circuit chamber and the expansion circuit chamber, a cyclic flow of media is generated across the hollow fiber membranes and through the extracapillary space of the bioreactor shown in FIG. 2. As the integration circuit chamber is pressurized above the expansion circuit chamber, media is pushed from the lumens of the fibers across the fiber membranes into the extracapillary space along the full length of the bioreactor. This bathes the cells in nutrient and oxygen rich media. As the expansion chamber is pressurized above the integration chamber, oxygen depleted media and waste by-products are moved from the expansion circuit, through the cell bed and finer membrane into the integration circuit. This process in continually repeated during the cell culture period and results in a substantially homogeneous environment. Unfortunately, as the media moves across the fiber from the integration chamber to the expansion chamber, cells are pushed out from the bioreactor into the expansion chamber. There the cells will settle out, become trapped and die.

SUMMARY OF THE INVENTION

The present invention provides a new and improved method for culturing cells in vitro which overcomes all of the aforementioned prior art limitations.

The present invention provides a new and improved process for improving mass transfer in a membrane bioreactor providing a more homogeneous culture environment by using an extracapillary circulation loop which provides a more homogeneous environment while eliminating the loss of cells in the expansion chamber of the above described pressure cycling system.

By circulating the cell side liquid, mixing is improved and the boundary layers or concentration gradients along the membrane and around the cells are reduced and the mass transfer is thereby improved. The circulation also more evenly distributes the high molecular weight molecules that are too large to cross the membrane.

The present invention provides a new and improved process for growing cells in a bioreactor, thus improving productivity of the apparatus which is exactly proportional to the mass transfer improvement.

The present invention provides a new and improved method using an apparatus for cell culture comprising at least one bioreactor of the type having a plurality of capillary tubes located within a shell with the opposite ends of the lumens of the capillary tubes being connected to a first circulation loop including a pump for circulating media, a device for oxygenating the media and adjustment of the small pH, a pH probe for monitoring and controlling pH and reservoir means for adding fresh media and factors and waste/effluent removal, and a second loop connected to opposite ends of the extracapillary space of said bioreactor including a pump for recirculating media through the extracapillary space, a device for assuring even flow through the extracapillary space of each bioreactor and media addition means with dilution means for gradient dilution or addition of extracapillary media components.

The new and improved method according to the present invention includes the circulation of media through the lumens of capillary fibers in at least one bioreactor while simultaneously circulating a second media through the extracapillary space of the bioreactor.

The foregoing and other objects, features and advantages of the invention will be apparent from the following more particular description of a preferred embodiment of the invention as illustrated in the accompanying drawings.

DETAILED DESCRIPTION OF THE INVENTION

Figure 1:
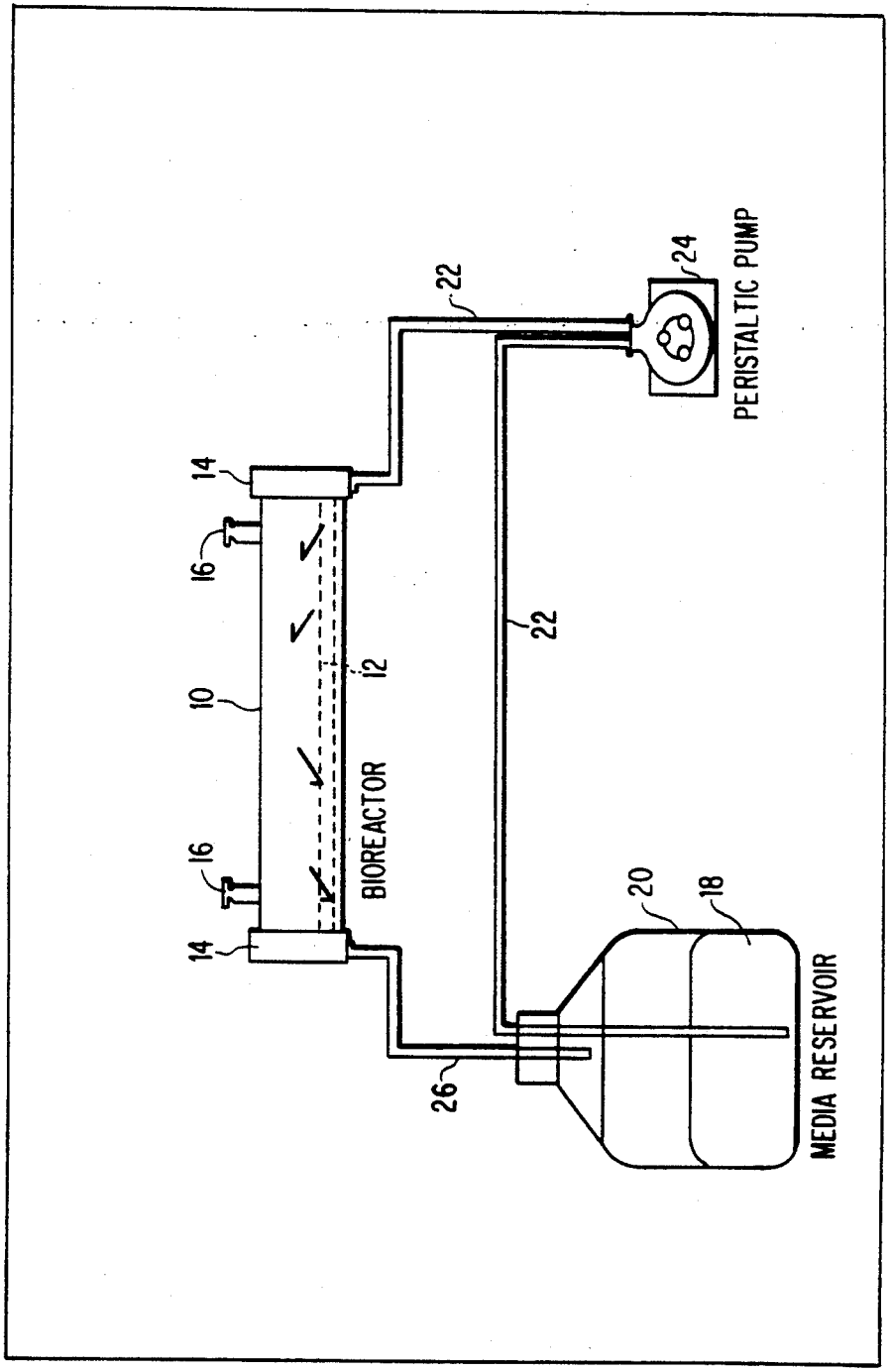
FIG. 1 is a schematic diagram of a conventional, prior art hollow fiber system for cell culture.

The conventional prior art system shown in FIG. 1 is comprised of a bioreactor 10 of the type having a plurality of hollow, capillary fibers 12, one of which is shown by dashed lines in FIG. 1, disposed parallel to each other with the opposite ends in communication with plenums 14. The extracapillary space within the reactor 10 is only accessible through at least closeable ports 16 located at at least one end thereof for the introduction of the cells to be cultured suspended in a cell growing media into the bioreactor. Media 18 from a suitable reservoir 20 is supplied to the capillary fibers 12 through tubing 22 by means of a peristaltic pump 24 and media is returned to the reservoir 20 through the tubing 26. While the media is passed through the lumens of the fibers, the extracapillary space within the bioreactor 10 is capped by closing the ports 16 so as to create a sealed environment.

Figure 2:
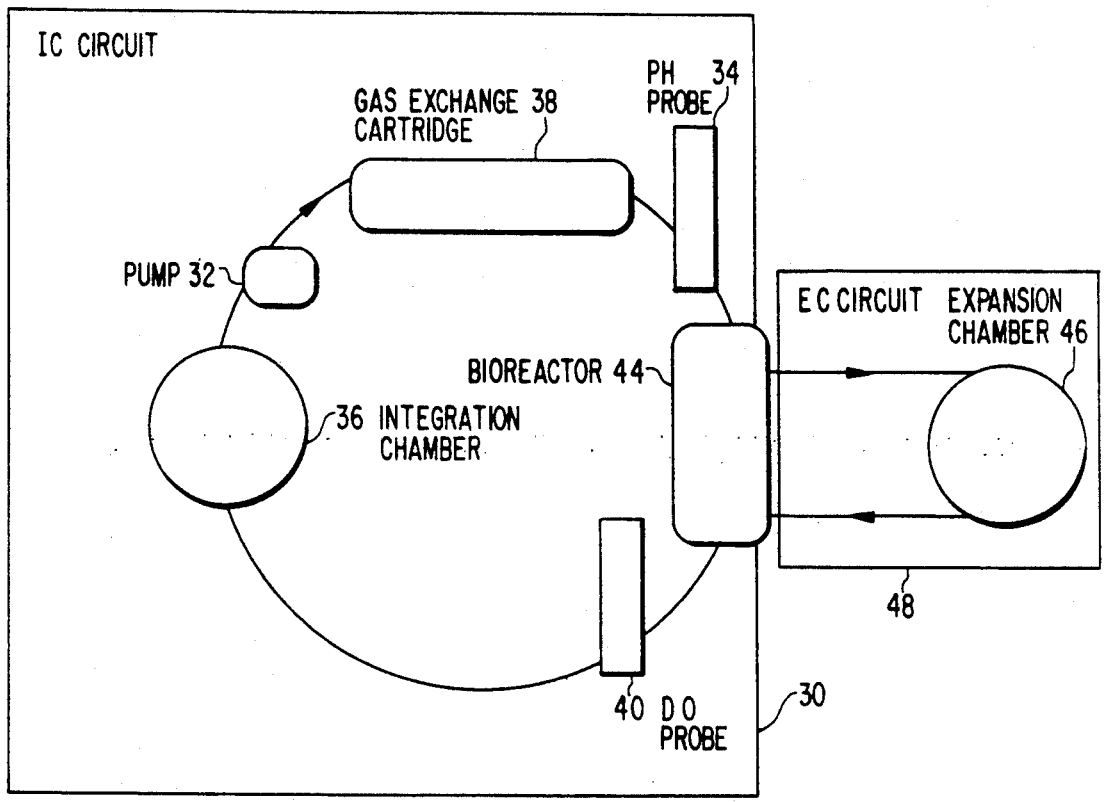
FIG. 2 is a schematic diagram of a prior art cycling system for cell culture.

The prior art cycling system, as shown in FIG. 2, presented an improvement over the hollow fiber technique disclosed in FIG. 1 since two fluid circuits are provided. The first fluid circuit is an integration circuit IC 30 which includes a bellows pump 32, a pH probe 34, an integration chamber 36, a gas exchange cartridge 38 and a DO probe 40 connected in series with opposite ends of the bioreactor 44 in communication with the hollow fiber membranes extending between the ends. The second fluid circuit is the expansion circuit EC 48 which connects the extracapillary space within the bioreactor 44 with an expansion chamber 46 containing additional media. By regulating the pressure differences between the integration chamber 36 and the expansion chamber 46, a cyclic flow of media is generated across the membranes within the bioreactor 44. As the integration circuit chamber 36 is pressurized above the expansion chamber 46, media is pushed from the lumen of the fiber across the fiber membrane and into the extracapillary space along the full length of the bioreactor. This bathes the cells in nutrient and oxygen rich media. As the expansion chamber 46 is pressurized above the pressure of the integration chamber 36, oxygen depleted media and waste by-products are moved out of the cell bed, through the fiber membrane and into the integration chamber circulation. This process is continuously repeated during the cell culture period and results in a homogeneous environment. However, as the media moves across the fibers from the integration chamber to the expansion chamber, cells are pushed from the bioreactor 44 into the expansion chamber 46 where the cells settle out, become trapped and die.

Figure 3:
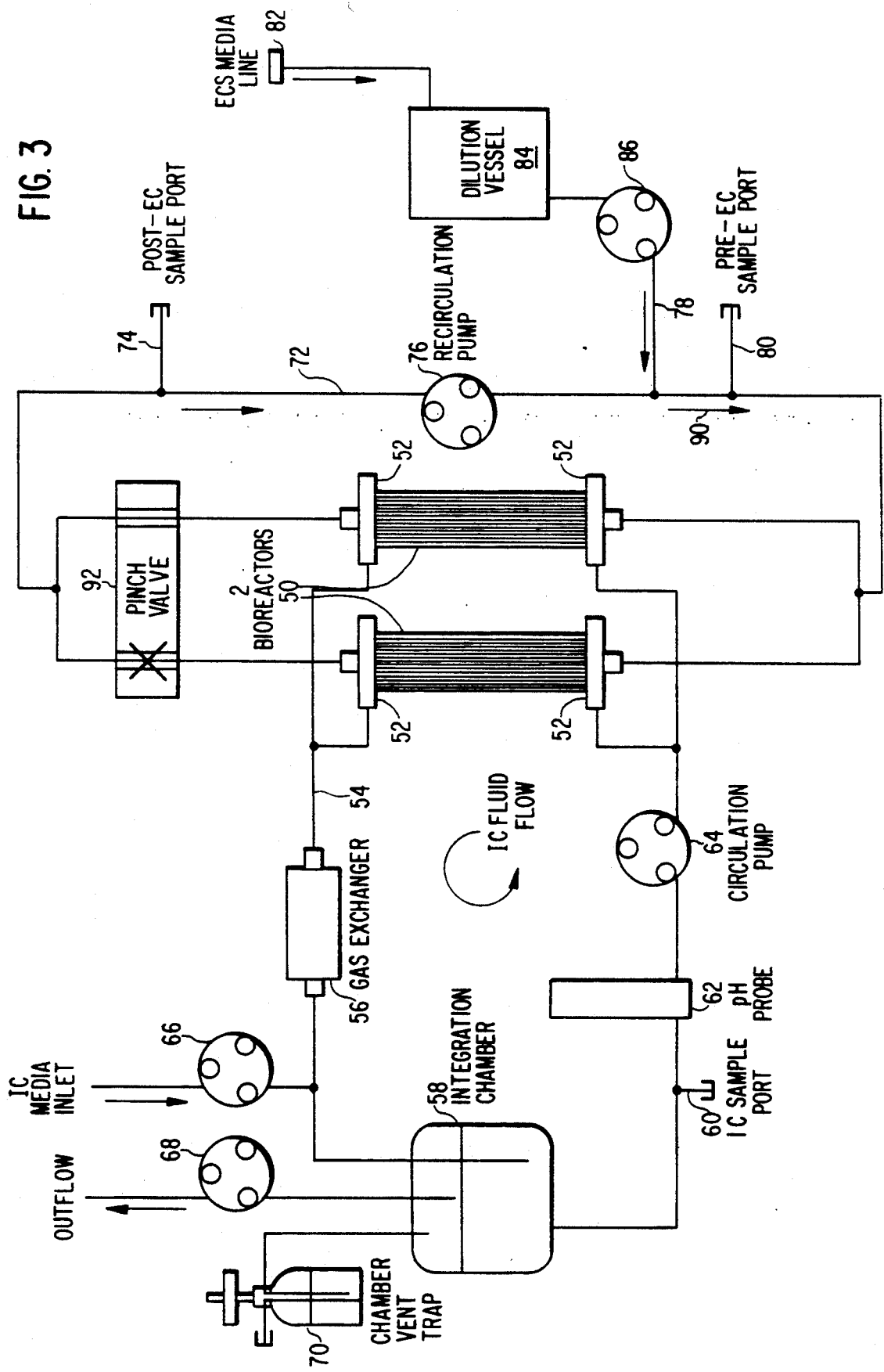
FIG. 3 is a schematic diagram of a cell culture system according to the present invention with an extracapillary circulation loop.

The tubing set according to the present invention as shown in FIG. 3, utilizes two bioreactors 50 which are connected in parallel with each other, both for the flow of media through the lumens of the capillary fibers and the flow of media through the extracapillary spaces. While two bioreactors have been shown in the example of FIG. 3, it is obvious that one bioreactor could be utilized or a greater number of bioreactors could be utilized. The plenum chambers 52 of the bioreactors 50 which are in communication with the lumens of the capillary fibers (not shown) are connected in series in an integration chamber circuit 54 with a gas exchanger 56, the integration chamber 58 an integration chamber sample port 60, a pH probe 62 and a circulation pump 64. Additional pumps 66 and 68 are provided for integration circuit media inlet and an outflow respectively. A chamber vent trap 70 is connected to the free space above the media in the integration chamber 58. The extracapillary space (not shown) in the bioreactors 50 are connected in series in an extracapillary recirculation circuit 72 with post-extracapillary sample port 74, a recirculation pump 76, a media inlet 78 and a pre-extracapillary sample port 80. The media inlet 78 provides for the introduction of extracapillary space media from a source 82 connected in series with a dilution vessel 84, a pump 86 and the media inlet port 78.

In the production of LAK or TIL cells, the cultureware set is sterilized and operated using normal hollow fiber growth techniques. Media is circulated through the integration chamber circuit 54 continuously. Cells (lymphocytes) are inoculated into the extracapillary space of the bioreactors 50 through the Pre EC sample port 80. When the cells are inoculated, the extracapillary recirculation pump 76 is stopped for a time (for example, two days) to allow the cells to settle onto the fibers. When the recirculation pump is again started, the factor pump 86 is also started to add fresh supplements such as serum free media and IL 2. The dilution vessel 84 attached to the extracapillary factor line assures a gradual introduction of the supplements so as not to shock the cells. Glucose and lactate are monitored off-line and media rates adjusted accordingly. When the cells reach confluence, the bioreactor can be removed and the cells harvested.

In the arrangement shown in FIG. 3, the recirculation pump 76 is only operable to pump the media in the direction of the arrows 90 and pinch valves 92 may be provided in the circuit to balance the flow of media through the two bioreactors. An alternative means for balancing the flow of media to multiple bioreactors is the use of dedicated peristaltic pumps for each bioreactor between each bioreactor and the pre-EC sample port 80.

Figure 4:
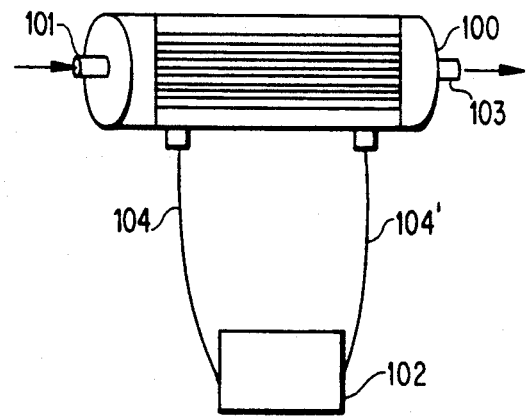
FIG. 4 is a schematic view of a first modified extracapillary recirculation loop according to the present invention.

A modified circuit arrangement for pumping the media through the bioreactors is schematically shown in FIG. 4. For the sake of clarity, only a bioreactor 100, a pump 102 and the connecting circuit 104 are illustrated for the sake of simplicity. The pump 102 is reversible so that the flow of media through the extracapillary space within the bioreactor 100 may be in either direction since the process works equally well with the flow in either direction. In fact, an improvement has been found if the flow of media through the extracapillary space of the bioreactor is periodically reversed, as will be discussed in greater detail hereinafter.

Figure 5:
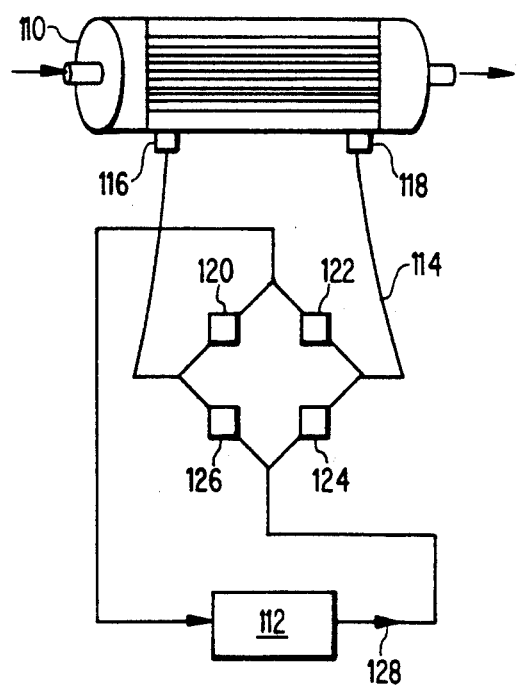
FIG. 5 is a schematic diagram of a second modified extracapillary recirculation loop according to the present invention.

In the embodiment of FIG. 5, a still further modified form of extracapillary recirculation circuit is illustrated schematically wherein the bioreactor 110 is connected to a pump 112 which is only operable to pump the media in a single direction. However, a switching circuit 114 is provided between the inlet and outlet ports 116 and 118 of the extracapillary space in the bioreactor 110 and the pump 112. The switching circuit 114 includes a diamond-shaped network having four valves 120, 122, 124 and 126 located in each branch. Since the pump 112 is always pumping the media in the direction of the arrow 128, the closing of the valves 120 and 124 and the opening of valves 122 and 126 will render the port 116 an inlet port and the port 118 an outlet port. Upon closing the valves 126 and 122 and opening the valves 120 and 124, the port 118 will be the inlet port and the port 116 will be the outlet port. The opening and closing of the valves and the timing thereof can be controlled automatically so that the flow of media through the extracapillary space within the bioreactor 110 can be automatically controlled in the desired sequence to promote cell growth.

While the bioreactor in the foregoing embodiments has been described as having a plurality of hollow capillary fibers, it is obvious that bioreactors comprised of sheet membranes could also be used with equal facility.

EXAMPLE ONE

A hollow fiber bioreactor (ACUCELL 1100 Endotronics, Inc. Minneapolis, Minn.) was operated according to the schematic in FIG. 4. Pure water was delivered to the inlet means (101) at a rate of 600 ml/hr and samples were taken from the outlet means (103) at five minute intervals. A glucose concentrate solution of 4000 mg % was introduced via a "T" connection in one of the conduit means (104) at a rate of 4 ml/hr and an equal amount was withdrawn from a "T" connection in the other conduit means (104'). Each circulation rate (4, 100, 200, 300, 400 ml/hr) was maintained for 135 minutes. The samples taken from the outlet means (103) were assayed for glucose concentration on an Abbott VP Chemistry Analyzer (Chicago, Ill.). Glucose removal rates and total glucose removed was calculated based on the lumenal flow rate and the glucose concentration of the sample. Clearance of glucose improved 1.38 fold from a 4 ml/hr circulation rate (22.5 mg) to 400 ml/hr circulation rate (31 mg). However, flow rates greater than 100 ml/hr provided minimal improvements of glucose clearance.

EXAMPLE TWO

In this experiment, the flow direction through the cell culture compartment was reversed at about 250 minutes. Glucose removal rate almost doubled. Thus, a preferred embodiment is the one in which the cell culture space circulation direction is reversed regularly. An optimum period for this particular bioreactor is about 10-15 minutes in each direction.

EXAMPLE THREE

Lymphokine activated killer (LAK) cell culture

IL-2 stimulated lymphocytes were cultivated in a hollow fiber bioreactor (hereinafter HFBRX) flowpaths that cycled or circulated and in static culture. For purposes of discussion, the day of inoculation was day 0 and day 1 was 24 hours later, etc. The media for these cultures was:

1. Basal feed medium (medium circulated through the fiber lumens)—RPMI-1640 with 3 g/L glucose, 50 ug/ml gentamicin sulfate and 4 mM glutamine. This medium was perfused through the fiber lumens for the duration of each culture.
2. Extracapillary space (ECS) medium—AIM-V (Gibco, Grand Island, N.Y.) with 1000 units IL-2/ml (Cetus).
3. ECS fiber coating medium—AIM-V with 5% human AB serum. 1000 units IL-2/ml (Cetus) (150 ml=ECS volume).

LAK cell cultures were performed simultaneously. The cultures were initiated from a split inoculum obtained from a single donor. The operating procedure for the HFBRX flowpaths and static culture controls are described below:

Prior to inoculation, the HBFRX cultureware was flushed and filled with 5 liters of basal media. Next, ECS circulation was initiated for each HFBRX and continued 24 hours prior to inoculation. This step allowed temperature and pH of the media to stabilize.

The ECS fiber coating medium was added 4 hours prior to inoculation. This medium, which contained serum and IL-2, displaced the basal medium in the ECS. The 10,000 MW cutoff of the hollow fibers retained the larger human serum components and IL-2 (approximately 14,000 MW) in the ECS of the HFBRX. Continued ECS circulation ensured uniform distribution of 1,000 units/ml IL-2 throughout the ECS.

The two systems and PL732 bags were inoculated simultaneously with leukapheresed peripheral blood lymphocytes, from one HTLV negative, Hepatitis B surface antigen negative, healthy donor ($1 \times 10^9$ cells/bioreactor=$2 \times 10^9$ cells/system).

Immediately following inoculation, ECS circulation was stopped to allow the cells to settle into the fiber bed. Medium flow in the ECS was not initiated until two days later, which allowed cells to adapt to their new environment. After that time, each system was operated in accordance with specific cultureware adaptations.

In addition, an ECS media feed was started on day 2 to replace and maintain adequate IL-2 levels for the duration of the culture. ECS medium (containing 1000 IU/ml IL-2) was added to the HFBRX from the dilution vessel at a rate of 10 ml/hr. IL-2 concentrations in the bioreactors were not determined.

Post bioreactor medium samples were withdrawn daily to determine glucose utilization and lactate production rates. The basal medium feed rate was adjusted accordingly to maintain predetermined metabolite levels. The cultures were maintained at pH 7.15 by computer-controlled regulation of carbon dioxide delivery to the gas exchange cartridge. Cells were harvested 14 and 24 days after inoculation by flushing cells from the bioreactor manually. After harvest, cell number, phenotype, viability and lytic activity were determined. The cytolytic activity was determined by a standard $^{51}Cr$ release assay. The target cells were the NK sensitive erythroleukemia tumor cell line K562, and the LAK sensitive B-lymphoblastoid cell line, Daudi.

Concurrent with each HFBRX culture, one liter gas permeable bags (PL732, Baxter Fenwal) were established at day 0 to serve as controls for LAK cell proliferation and activation. Two bags were inoculated at a cell density of $3.0 \times 10^6$/ml in the same media used in the ECS of the bioreactors (described above). The bags were filled to a volume of 400 mls/bag ($1.2 \times 10^9$ mononuclear cells/bag). Serum was maintained for the duration of these cultures. The bags were then harvested and fed on days 7 and 17, and finally harvested on day 24. The rationale for beginning the cultures in the bags at $3.0 \times 10^6$/ml was to insure activation of the cells before they enter the expansion phase (between days 7-10). When the bags were fed at days 7 and 17, counts and calculations were carried out to determine the amount of media necessary to adjust to a cell density to $0.5 \times 10^5$/ml. Thus, days 7 and 17, a certain amount of conditioned media was left in the bags and simply diluted with fresh media. This is not uncommon and has been shown to be important for the expansion of lymphoid cells. In most cases, the amount of conditioned media consumed was between 10% and 25%.

TABLE 1

Expansion of LAK cells in control and experimental HFBRX flowpaths and PL732 controls bags.

| | Viable Cell Number (%)[a] | | |
|---|---|---|---|
| Day | PL732 Bags (cells/ml) | Circulated | Cycled |
| 0[b] | $3.0 \times 10^6$ (98%) | $2.0 \times 10^9$ (98%) | $2.0 \times 10^9$ (98%) |
| 14 | ND[c] | $1.0 \times 10^{10}$ (84%) | $2.1 \times 10^9$ (88%) |
| 24 | $1.0 \times 10^6$ (96%) | $1.5 \times 10^{10}$ (81%) | $1.7 \times 10^9$ (64%)[d] |

[a]Percent viable of total cell number.
[b]Each flowpath was inoculated with $1.0 \times 10^9$ mononuclear cells per HFBRX. Each PL732 bag was inoculated with $1.2 \times 10^9$ cells and average of both bags is listed.
[c]Not determined.
[d]On day 24, cells were recovered from the HFBRX of BFP1 ($1.7 \times 10^9$, 64% viable) and from the EC chamber ($6.4 \times 10^9$ cells, 37% viable).

According to the data summarized in Table 1, the HFBRX flowpath modified to contain an ECS circulation loop generated the greatest cell proliferation. A lower cell recovery was observed in the control flowpath which incorporated an expansion chamber and ECS cycling. The data indicate that, for LAK cell culture, ECS homogeneity can be adequately maintained by simple mechanisms other than ECS cycling.

Concurrently, two PL732 bags were inoculated at $3 \times 10^6$ cells/ml. The cell density in the cultures was reduced to $0.5 \times 10^6$ cells/ml on day 7, just prior to the expansion phase. The cultures were fed at days 7 and 17. According to that growth pattern 64 bags, 32 liters of enriched medium (AIM V, 10% human serum, 1000 units/ml IL-2) and $32 \times 10^6$ units of IL-2 would be required to generate $10^{11}$ LAK cells. There would also be a tremendous labor burden to feed and harvest that number of bags. By comparison, significantly less resources are required to generate a therapeutic cell number in HFBRx flowpaths. Approximately 5 liters of enriched media, $5 \times 10^6$ units IL-2, and significantly fewer man-hours were required to support these cultures.

A standard 4 hour $^{51}Cr$ release assay (Yannelli et al. (1988) Canc Res 48:5696) was used on days 14 and 21 to determine the functional state of the expanded LAK cells. The targets used were K562, Daudi and A375 cells, which are available from the ATCC in Rockville, Md. Cells from the three treatments were competent in lysing each of the target cells.

The composition of the cell populations was determined by flow cytometric analysis using antibodies directed to cell surface antigens. The distribution of the cell surface antigens is characteristic of the different cell types. The labelled antibodies used were purchased from Coulter Immunology, Hialeah, Fla. and were specific for the antigens CD4, CD8, TA2, NKHI, Leull and CD25.

The cells were adjusted to a concentration of $1 \times 10^6$/ml and incubated with the antibodies at saturating dilutions for 30 minutes at 4° C. The cells were washed and analyzed on an cytofluorograph (Ortho Diagnostics). The relative properties of cytotoxic (CD3+/CD8+) and helper (CD3+/CD4+) T cells, NK cells (total and activated) and total activated T cells and NK cells were similar among the three treatments over a period of 24 days.

EXAMPLE FOUR

The cultureware was installed according to FIG. 3 and flushed with 5L of Gibco McCoy's 5A then maintained for three days at a feed rate of 30 ml/hr and circulation rate of 100 ml/min.

Fresh McCoy's containing 4 mM 1-glutamine was fed to the system one day prior to inoculation at a rate of 50 ml/hr. A 50 ml IC and 20 ml EC sample were obtained and used for cytotoxicity and sterility testing. The samples revealed that the system was sterile.

A 15 ml bolus injection of fetal bovine serum was added to the EC circuit and the EC circulation pump (Masterflex model #7520-30) was started and calibrated to 50 ml/hr to homogenize the EC.

Inoculation occurred five hours after serum treatment. A 40 ml inoculum of a murine hybridoma that secretes an IgG antibody, containing $3.168 \times 10^8$ cells at 97% viability, was prepared. Each bioreactor received 20 ml of inoculum followed by a 5 ml medium flush. The EC circulation pump was turned off.

A unidirectional EC circulation of 50 ml/hr was initiated on day 2.

Daily EC samples were taken starting day 7 to determine cell number and viability in the circulation loop. Harvesting was also initiated on this day at 3 ml/hr.

TABLE TWO

| Day of Sample | Viable Cell count ($\times 10^6$ ml) | Viability | EC Circ. Rate (ml/hr) |
|---|---|---|---|
| 07 | 4.84 | 39% | 50 |

TABLE TWO-continued

| Day of Sample | Viable Cell count ($\times 10^6$ ml) | Viability | EC Circ. Rate (ml/hr) |
|---|---|---|---|
| 08 | 9.56 | 86% | 50 |
| *09 | 33.30 | 83% | 50 |
| 12 | 66.00 | 85% | 100 |
| 13 | 46.75 | 85% | 58 |
| 14 | 22.60 | 83% | 58 |
| 15 | 18.40 | 84% | 58 |
| 16 | 17.70 | 83% | 58 |
| 17 | 30.00 | 77% | 58 |
| 18 | 33.80 | 80% | 58 |
| 19 | 28.00 | 77% | 58 |
| 20 | 21.00 | 81% | 58 |

*One bioreactor was removed from system after cell count.

Cells were removed from a bioreactor with a simple flush of medium through the EC using a masterflex pump. The bioreactor was inoculated with $1.584 \times 10^8$ cells. After 9 days, $2.65 \times 10^{10}$ cells were removed at 54% viability. That represents a 167-fold increase in cell number.

Harvesting took place from culture day 7 to culture day 20. During that time, a total of 5.831 grams of murine IgG was collected in 1693 ml, translating to an average antibody production of 292 mg/day.

While the invention has been particularly shown and described with reference to preferred embodiments thereof, it will be understood by those in the art that the foregoing and other changes in form and details may be made therein without departing from the spirit and scope of the invention.

What is claimed is:

1. A process for improving mass transfer between a liquid source medium and a liquid medium containing cells in a membrane bioreactor comprising:
    circulating the liquid media through at least one bioreactor having at least one semi-permeable membrane and simultaneously circulating the second liquid media inoculated with a cell culture through said at least one bioreactor on the opposite side of said membrane.

2. A process as set forth in claim 1, further comprising circulating said first liquid media in a first circuit through an integration chamber, a gas exchanger, and a pH probe by means of a circulation pump all disposed in series with said at least one bioreactor.

3. A process as set forth in claim 2, further comprising circulating said second liquid media in a second circuit and introducing additional media through a dilution vessel into said second circuit containing said second liquid media.

4. A process as set forth in claim 1, further comprising circulating said first and second liquid media through a plurality of bioreactors connected in parallel while independently controlling the flow of said second liquid media through each bioreactor to provide a balanced flow through each bioreactor.

* * * * *